United States Patent [19]

Johnson

[11] Patent Number: 5,438,863
[45] Date of Patent: Aug. 8, 1995

[54] UNIVERSAL MATERIAL TEST SYSTEM AND METHOD

[75] Inventor: Jeffrey W. Johnson, N. Lawrence, Ohio

[73] Assignee: The B.F. Goodrich Company, Akron, Ohio

[21] Appl. No.: 56,711

[22] Filed: May 3, 1993

[51] Int. Cl.⁶ .............................................. G01N 11/04
[52] U.S. Cl. ................................... 73/54.02; 73/150 A
[58] Field of Search ..................... 73/54.02, 54.14, 81, 73/82, 150 A, 826, 827, 834, 818, 821, 805

[56] References Cited

U.S. PATENT DOCUMENTS

| | | | |
|---|---|---|---|
| 2,011,862 | 8/1935 | Konheim et al. | 73/54.14 |
| 2,076,592 | 4/1937 | Rhodes | 73/54.14 |
| 4,096,739 | 6/1978 | Barker et al. | 73/54.14 |
| 4,637,252 | 1/1987 | Rhee et al. | . |
| 4,680,958 | 7/1987 | Roelle et al. | 73/54.14 |
| 4,807,465 | 2/1989 | Botzolakis et al. | 73/821 |
| 5,140,861 | 8/1992 | Gleason et al. | 73/81 |
| 5,201,230 | 4/1993 | Sakakibara | 73/827 |

FOREIGN PATENT DOCUMENTS

| | | | |
|---|---|---|---|
| 2491213 | 4/1982 | France | . |
| 57-184951 | 11/1982 | Japan | . |
| 681197 | 10/1952 | United Kingdom | 73/54.14 |
| 1363643 | 8/1974 | United Kingdom | . |
| 171663 | 7/1965 | U.S.S.R. | . |

Primary Examiner—Robert Raevis
Attorney, Agent, or Firm—Renner, Otto, Boisselle & Sklar; Nestor W. Shust

[57] ABSTRACT

A universal test system for determining material properties of a specimen includes a base; a force sensing element in a fixed relative position to said base; a sample holder in a fixed relative position to said force sensing element, the sample holder adapted to receive a sample; a vertically movable element for contacting the sample in the sample holder and exerting a force thereon; and a controller for controlling the vertical position of the vertically movable element; wherein the force sensing element transfers an indication of the force exerted on the sample by the vertically movable element to the controller and wherein the controller controls the position of the vertically movable element in accordance with the indication of force sensed by the force sensing element.

11 Claims, 10 Drawing Sheets

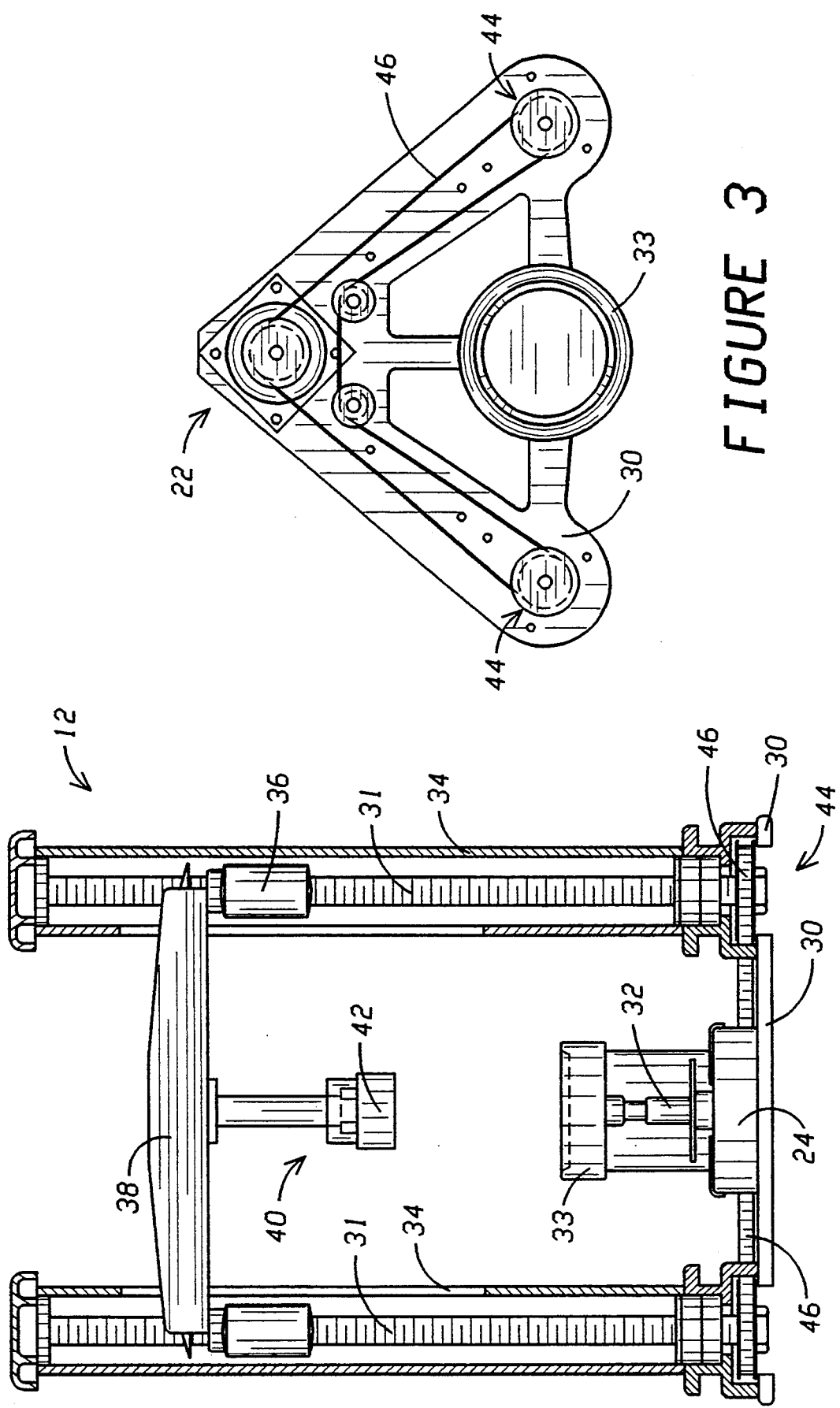

UNIVERSAL MATERIAL TEST SYSTEM AND METHOD

FIELD OF THE INVENTION

The present invention relates generally to a method and apparatus for determining certain material properties of a specimen, and, more particularly, to an automated method and apparatus for determining material properties of an elastomeric material.

BACKGROUND OF THE INVENTION

There are many known tests for determining material properties of a specimen, such as an elastomer. Some of these tests measure tack free time, adhesion and cohesion, extrusion rate, indentation hardness, adhesion-in-peel, etc. Unfortunately, many of these tests are cumbersome, inaccurate, and require significantly different test fixtures and procedures.

For example, the ASTM test for determining tack free time includes preparing a specimen of an elastomeric material and curing it for a given period of time. A strip of polyethylene plastic film is then placed on top of the specimen and held down by a brass weight for 30 seconds. The plastic film is then slowly pulled away from the specimen using the thumb and forefinger over 15 seconds. If no material remains affixed to the plastic film then the tack free time is something less than the time over which the speckmen was allowed to cure. If any material remains affixed to the plastic film, then the tack free time had not been reached and the area over which the material covers is measured and noted. This test is difficult to perform and the results are heavily subject to variances in the performance of the test.

Measuring one of the other material properties of the specimen typically requires a testing procedure and testing apparatus significantly different than that used for the tack free time test described above.

Devices exist which facilitate or simulate the determination of some material properties, but typically such a device is suitable for testing only one material property and a separate device must be employed for each different material property for which testing is to be performed. These devices are often bulky making it difficult to transport them.

It would be desirable to provide a testing device and method which is accurate and could be easily adapted to perform a variety of material tests.

SUMMARY OF THE INVENTION

The present invention allows a variety of material tests to be performed easily and accurately with minimal change required to the system to perform different tests.

In accordance with one aspect of the present invention a system for determining material properties of a sample includes a testing device, having a base, a load sensing element, a motor and a test apparatus, the test apparatus being adaptable to perform different material tests; a controller for controlling the functioning of the testing device; and a processor for processing the results of the test as sensed by the load cell; wherein the controller operates said motor to cause required movement of at least part of the test apparatus in accordance with a selected test.

In accordance with another aspect of the present invention, a system for determining material properties of a specimen includes a base; a force sensing element in a fixed relative position to the base; a sample holder in a fixed relative position to the force sensing element, the sample holder adapted to receive a sample; a vertically movable element for contacting the sample in the sample holder and exerting a force thereon; and a controller for controlling the vertical position of the vertically movable element; wherein the force sensing element transfers an indication of the force exerted on the sample by the vertically movable element to the controller and wherein the controller controls the position of the vertically movable element in accordance with the indication of force sensed by the force sensing element.

In accordance with a further aspect of the invention, a method for determining material properties of a sample includes the steps of placing a sample into a first recess in a fixed position above a load cell, exerting a force upon the sample, detecting the difference in load the sample exerts upon the load cell, and sampling and recording the difference in the load exerted upon the load cell.

In accordance with still another aspect of the invention, a method for determining material properties of a sample includes the steps of securing into a testing apparatus a first element having a recess adapted to facilitate the determination of a first material property, placing a sample into the recess of the first element, exerting a force upon the sample, detecting the response of the sample to the force, calculating a first material property based upon the detected response, replacing the first element in the testing apparatus with a second element having a recess adapted to facilitate the determination of a second material property, placing a sample into the recess of the second element, exerting a force upon the sample, detecting the response of the sample to the force, and calculating a second material property based upon the detected response.

The foregoing and other features of the invention are hereinafter fully described and particularly pointed out in the claims, the following description and the annexed drawings setting forth in detail a certain illustrative embodiment of the invention, this being indicative, however, of but one of the various ways in which the principles of the invention may be employed.

BRIEF DESCRIPTION OF THE DRAWINGS

In the annexed drawings:

FIG. 2 is an elevation of one embodiment of the test fixture of the system of the present invention such as for performing tack, adhesion cohesion tests, etc.;

FIG. 3 is a partial view of the test fixture of FIG. 2 illustrating the motor and drive mechanism of the test fixture;

DETAILED DESCRIPTION OF THE PREFERRED EMBODIMENT OF THE INVENTION

Figure 1:
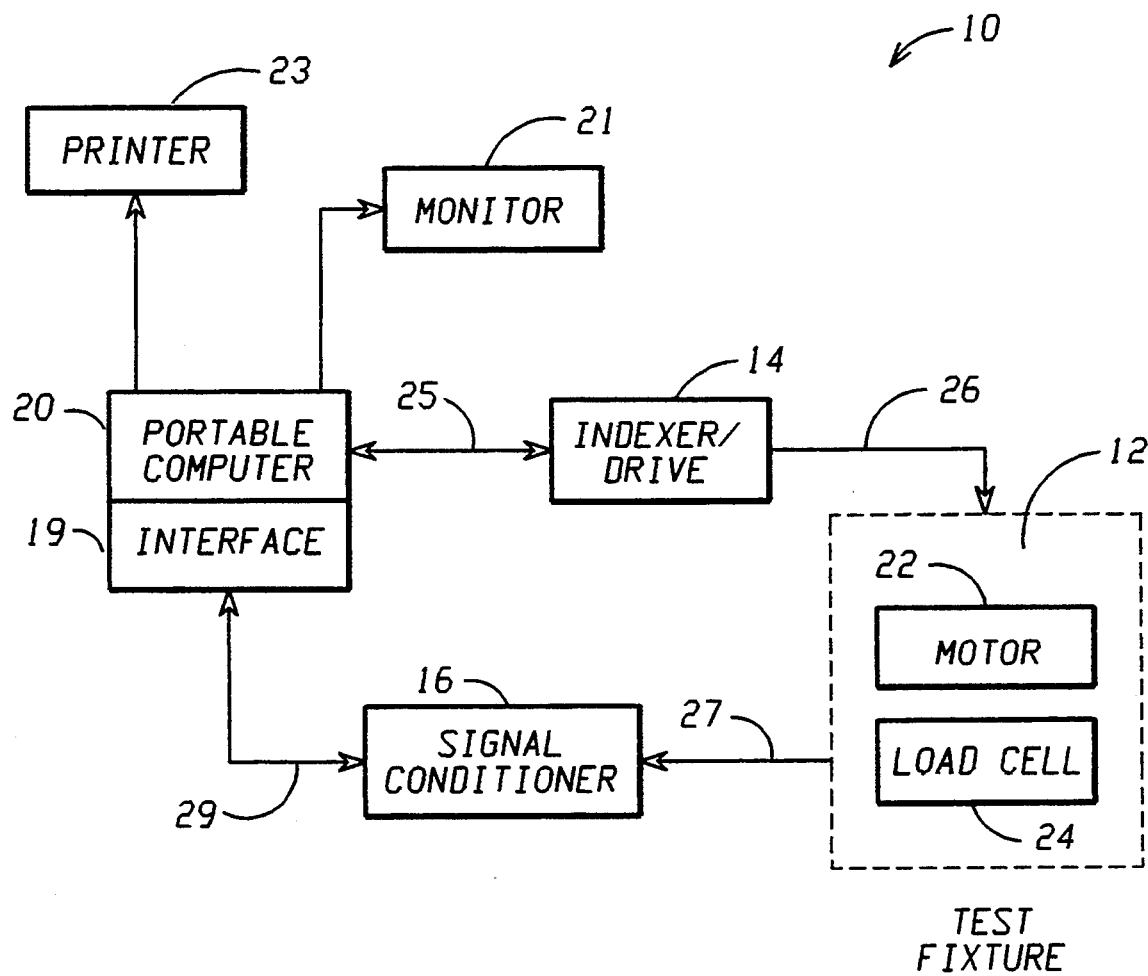
FIG. 1 is a block diagram of the portable universal material test system of the present invention.

With reference to the figures, and initially to FIG. 1, there is shown a portable universal testing system 10 constructed in accordance with the present invention. The testing system includes a test fixture 12, a drive controller 14 which controls the test fixture, a signal conditioner 16 which conditions the output from the test fixture and forwards it to an interface 19 which converts analog data to digital data for use by a computer 20. The computer 20, in addition to processing digital test data from the interface 19 also controls the overall test functioning of the system 10 through commands to the drive controller 14. Preferably, a monitor 21 and printer 23 are coupled to the computer 20 to provide a visual display as well as hard copy of the output including numerical and graphical output data.

The test fixture 12 includes a motor 22 for accomplishing the movement requirements of a specified testing procedure, a load cell 24 for sensing, as a change in load, the material characteristics of the specimen being tested, and other components which will be described more fully below which interact to carry out the desired test procedure. A motor which is suitable for many applications of the test fixture 12 is a Superior Electric M062-CE09 stepping motor. An exemplary load cell is a Kulite TC-2000/100 lb. load cell, although the force generated by the actual testing parameters and/or other operating requirements will dictate the specific load cell chosen.

The computer 20 is preferably a IBM compatible INTEL 286, 386 or 486 based microcomputer, such as a desk top or lap top computer, although the use of other processing units is possible. In some instances the monitor 21 may be a part of the computer, such as is usually the case when a laptop computer is employed. Preferably the computer 20 is portable to facilitate transportation of the system 10 to different locales or environments. The portable computer 20 acts as the interface with the user, as an overall system controller for initiating a desired test at the desired parameters and as a device for collecting test data and conveying the test data into information available to the user. To initiate a test and control the operation of the test fixture 12, the portable computer 20 communicates the required instructions to the drive controller 14 over an RS 232 serial bus 25. The drive controller 14 contains suitable circuitry for conveying instructions from the portable computer 20 into a format suitable for driving the motor 22 of the test fixture 12. One exemplary drive controller employs a Superior Electric 230-PI controller. The converted instructions are provided to the motor 22 via a control line 26.

The signal conditioner 16 receives output generated by the load cell 24 of the test fixture 12 over the line 27 during the test initiated and controlled by the portable computer 20. The output of the load cell 24 is a low level transducer signal which the signal conditioner 16 amplifies and conditions, such as through a Metrabyte EXP-16 signal conditioning card. For example, the signal conditioner 16 provides a five volt excitation voltage to the load cell 24 and conditions the output signal from the load cell at a gain of 100. The gain is selected based on the plus/minus five volt input to the interface 19, for example an SAS8 interface card, and can be adjusted for load cells with different output levels. As an example using the mentioned components, the output signal level of the exemplary Kulite TC-2000 load cell and the gain produced by the exemplary Metrabyte EXP-16 signal conditioner 16 results in a resolution of 0.035 pounds. The amplified and conditioned signal is transferred to the portable computer 20 over line 29 through the interface 19 which includes an analog to digital converter and clock timing circuit enabling the appropriate conversion. The interface 19 may be a Metrabyte DAS8 card which can be inserted into an available slot in the portable computer 20 or any other interface circuitry which performs similar functions.

In operation, the portable computer 20 will initiate a series of instructions to the drive controller 14 which drives the motor 22 in an appropriate manner to conduct the selected test. The results of the test as detected by the load cell 24 are then passed to the signal conditioner 16 where they are amplified and conditioned and forwarded to the interface 19 which turns the amplified transducer signal from the load cell 24 into digital form for use by the portable computer 20. The portable computer 20 then processes the data, correlates it with data from other test runs and provides suitable numerical and graphical output, such as through a display or a printer.

One construction of a test fixture 12 suitable for performing tack free time tests and adhesion and cohesion tests in particular is shown in FIGS. 2 and 3. FIG. 2 depicts an elevation of the test fixture 12. The test fixture 12 includes a base 30 upon which is mounted the load cell 24 and a pair of vertically extending threaded shafts 31. Affixed atop the load cell 24 is a fixture adaptor 32 which permits different fixtures to be positioned above the load cell 24 for a variety of different tests. In the example of a tack test, the fixture 33 to be used will typically be in the form of a brass cup having a small annular recess for holding a predetermined amount of elastomeric material therein. For other material tests the fixture 33 will be different, such as a chamber adapted to receive a plunger and having an aperture for an extrusion rate test.

Encompassing each vertically extending threaded shaft 31 is a tubular housing 34 sized to permit the axial movement therein of a nut 36 in threaded connection with the threaded shaft. Attached to each nut 36 through an axial slit extending substantially the length of each housing 34 is a central carriage 38 with a downwardly extending upper fixture 40. In the instance of a tack testing fixture the upper fixture 40 will include a block 42 having a known area which is smaller than the recessed area of the cup 33. The block 42 may be made of brass or glass or of a construction material, such as concrete, with which the specimen would be used in actual practice. In some instances the block may include a recess into which a sample material may be applied.

The threaded shafts 31 are journalled within the tubular housings 34 so as to be rotatable therein when driven by the motor 22. The shafts 31 at their bottom most extent include a pulley assembly 44 which places the threaded shafts 31 into communication with the motor 22 via a continuous belt 46. Rotation of the motor 22 causes the belt 46 to travel along a path, as shown in FIG. 3, which causes both threaded shafts 31 via their connections to pulleys 44 to rotate in the same direction. Rotation of the threaded shafts 31 causes the nuts 36 and in turn the central carriage 38 to travel up or down along the threaded shafts as determined by the drive direction of the motor 22.

Vertical movement of the carriage 38 is performed by a sequence of instruction codes down loaded from the portable computer 20 to the motor drive controller 14 over the RS 232 bus 25. The motor drive controller 14 translates these instructions into driving signals operating the motor 22 in a half step mode. The motor driving signals, which are communicated to the motor 22 over the line 26, subdivide the rotation of the motor, and thus of the threaded shafts 31, into 400 increments per one rotation of the motor. Using threaded shafts having a pitch of for example 10, or 10 revolutions per one inch, the vertical distance resolution of the carriage 38 is thus 0.25 milliinches. The motor drive controller 14 maintains an internal counting register which keeps track of the relative vertical position of the carriage 38 at any time during operation. The relative position or displacement of the carriage 38 is provided from the motor drive controller 14 to the portable computer 20 over the RS 232 bus 25.

In a tack free time test operation, an operator will fill the recess of the cup 33 with a sample of an elastomeric material and strike off material extending above the upper surface of the cup using a straight edge to provide a level surface of elastomeric material. After the elastomeric material in the cup has been allowed to cure for a predetermined length of time, the operator enters the appropriate commands on a keyboard to instruct the portable computer 20 to begin the test. Instruction codes are then down loaded from the portable computer 20 to the computer drive controller 14 over the RS-232 bus 25 and the instructions are convened into motor drive signals. The motor 22 then turns the threaded shafts 31 to move downwardly the central carriage 38 until the block 42 contacts the sample in the cup 33. Upon the block 42 contacting the sample and exerting a force thereon, the force is transferred to the load cell 24 via the lower fixture 32. The load cell 24, based on the 5 volt excitation signal received from the signal conditioner 16, will translate the force into an output signal with a voltage corresponding to the exerted force. The signal conditioner 16 conditions and amplifies the load cell output signal received over line 27 and sends it to the portable computer 20 through the interface 19 and over line 29.

Based on the force detected by the load cell 24 and the cross sectional area of the block 42, the portable computer 20 can compute the pressure exerted on the sample by the block. The portable computer 20 will continue sending instructions to the motor 22 to lower the block 42 until the portable computer 20 determines based on the force sensed by the load cell 24 that a predefined contact pressure between the block and the sample has been achieved. Once the predefined contact pressure has been reached, the portable computer 20 will allow the block 42 to dwell in the contact position maintaining the predetermined pressure on the sample for a preset time, such as one second. Alternatively, once the block 42 was detected as exerting the predetermined pressure on the sample, further monitoring of the pressure for the purposes of adjusting the block could be discontinued. At the end of the dwell time, the portable computer 20 will command the motor 22, through the drive controller 14, to raise the central carriage 38 and block 42 at a preset speed of, for example, 10 inches per minute. During the initial one-half inch of travel of the block 42 away from the cup 33, the amplified and conditioned output of the load cell 24 is sampled by the interface 19 at a rate of 25 hz and provided to the portable computer 20 which stores the sampled load data. After the carriage 38 and block 42 have been raised away from the cup 33 by one-half inch, the carriage is returned to its standby position at a quicker rate.

Figure 4:
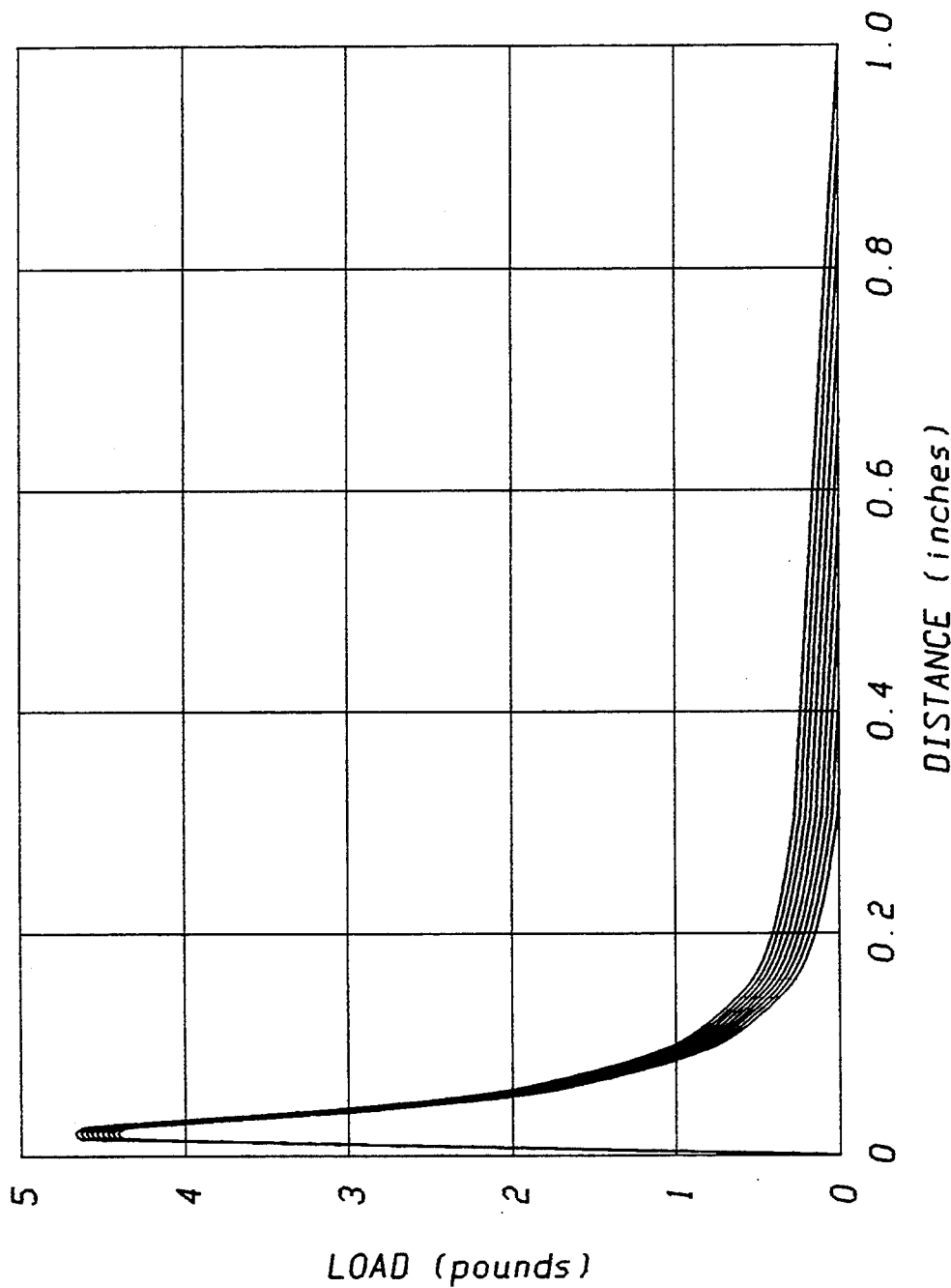
FIG. 4 is a graph of load as a function of distance for an exemplary tack free time test.

The portable computer 20 correlates the load values sampled during the initial one-half inch pull away distance with the corresponding displacement distance from the sample, as supplied by the drive controller 14, and the results are plotted, such as on a computer screen. An exemplary plot of load detected by the load cell 24 as a function of the displacement distance of the block 42 from the sample is represented by one of the several plots of FIG. 4. Total energy is then calculated by integrating the load force over the one-half inch test distance. The tack value is yielded by dividing the calculated energy by the test sample contact area. These calculations are stored and can be printed out on hard copy upon demand. Data generated from several tests can be accumulated and plotted together to facilitate comparison, for example as is shown in FIG. 4. The output for nine tests performed after 2, 5, 10, 15, 20, 25, 30, 35 and 40 minute curing times for an exemplary material, such as an elastomer, is shown in FIG. 4 and in Table 1 below.

Referring to Table 1, the tack measured in lb-inches-/$in^2$ increases as curing time increases until the material has cured to such an extent that the surface of the material forms a skin and the material no longer remains affixed to the block 42 once it is pulled away from the sample. For the tests performed in Table 1, this occurred for test number 9 and thus the tack free time is likely between the curing times for samples 8 and 9. By plotting the tack values from Table 1 as a function of sample number or curing time, and performing a simple curve-fitting technique, the tack free time can be accurately determined as corresponding to the point on the plot where tack first begins to decrease from its maximum value.

TABLE 1

| SAMPLE | PEAK (lbs) | PEAK (psi) | ENERGY (lb-in) | TACK (lb-in/in2) | |
| --- | --- | --- | --- | --- | --- |
| 1 | 3.15 | 3.36 | 0.214 | 0.228 | |
| 2 | 3.67 | 3.92 | 0.217 | 0.232 | |
| 3 | 4.40 | 4.69 | 0.242 | 0.258 | |
| 4 | 3.96 | 4.22 | 0.248 | 0.264 | |
| 5 | 4.04 | 4.31 | 0.257 | 0.274 | |
| 6 | 3.70 | 3.95 | 0.273 | 0.291 | |
| 7 | 3.70 | 3.94 | 0.323 | 0.344 | |
| 8 | 3.86 | 4.12 | 0.369 | 0.394 | |
| | | | | TACK FREE | |
| 9 | 3.99 | 4.26 | 0.235 | 0.251 | |
| AVE CURVE | 3.71 | 3.96 | 0.26 | 0.28 | STD 0.055 |

A review of the tabulated results of Table 1 and the graphical results of FIG. 4 indicates that the material test system of the present invention provides a testing procedure which measures tack and tack-free time without introducing the random errors and uncontrollable variables often associated with the standard techniques. The results can be used accurately to predict the tack at various curing times under various environmental factors.

The test fixture 12 of the portable universal material test system 10 of the present invention can also be readily reconfigured to perform other material tests by replacing the cup and block 42 with appropriate elements to perform the desired test. For a constant force rheometry flow test or extrusion rate test, for example, the cup 33 would typically be replaced with a chamber having an orifice of a diameter suitable for permitting controlled flow of a sample material therethrough. The top of the chamber would be adapted to receive a plunger like device, which takes the place of the block 42 of the tack free time test apparatus. In such a test the chamber is filled with a sample and the carriage 38 is lowered until the plunger contacts the sample material in the chamber, as is detected by monitoring the output of the load cell 24. As the sample material begins to flow through the orifice due to the force exerted by the plunger, the motor is stepped to maintain a constant force on the sample material for a given time or distance of travel of the plunger after contact with the sample material. Based on the displacement data for the plunger, the force applied by the plunger, and the size of the orifice, flow characteristics for the material can be calculated.

Figure 5:
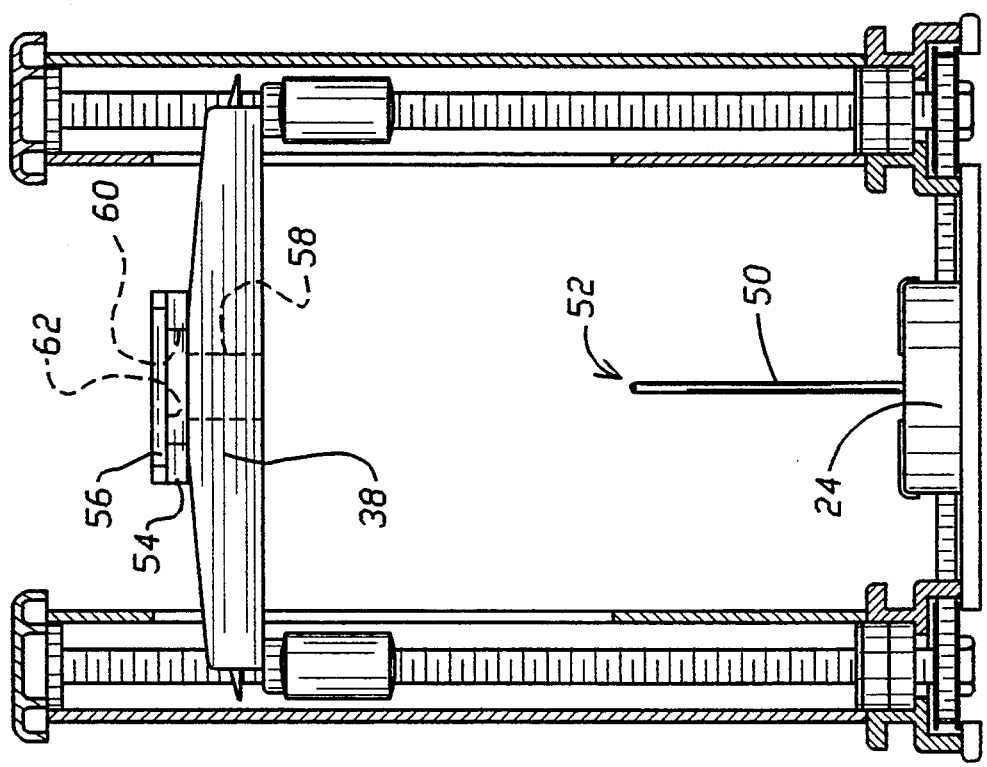
FIG. 5 is an elevation of the test fixture configured to perform an adhesion test for a pressure sensitive material.

The test fixture 12 can also be reconfigured to perform an adhesion test for a pressure sensitive material, as shown in FIG. 5. In this instance, the fixture adaptor 32 is removed and replaced with a vertical rod 50 of a relatively small diameter, for example 5 millimeters, with a polished end 52. The vertical rod 50 may be attached to the load cell 24 in the same manner as the fixture adaptor 32. The upper fixture 40 and block 42 are also removed from the central carriage 38. Placed atop the central carriage 38 is a support 54 and test plate 56. The carriage 38 and support 54 each include a passage 58 and 60, respectively, allowing the vertical rod 50 to pass therethrough and to contact the bottom surface 62 of the test plate 56 when the carriage 38 is lowered. To perform a test, a pressure sensitive adhesive is placed on the bottom surface 62 of the test plate 56 in an area within the passage 60 so as not to contact the support 54. The portable computer 20 will then initiate the appropriate set of instructions to the drive controller to cause the motor 22 to lower the carriage 38 until the polished end 52 of the vertical rod 50 contacts the pressure sensitive adhesive applied to the bottom surface 62 of the test plate 56 with the appropriate pressure. The motor 22 then begins to raise the carriage 38 and the pressure, as detected by the load cell 24, required to separate the test plate 56 having the adhesive material applied thereto from the rod 50 is detected and recorded. Preferably, the support 54 and test plate 56 are horizontally moveable upon the upper face of the carriage 38 so that the test may be repeated a number of times using different areas of the pressure sensitive adhesive applied to the bottom surface 62 of the test plate 56.

Figure 6:
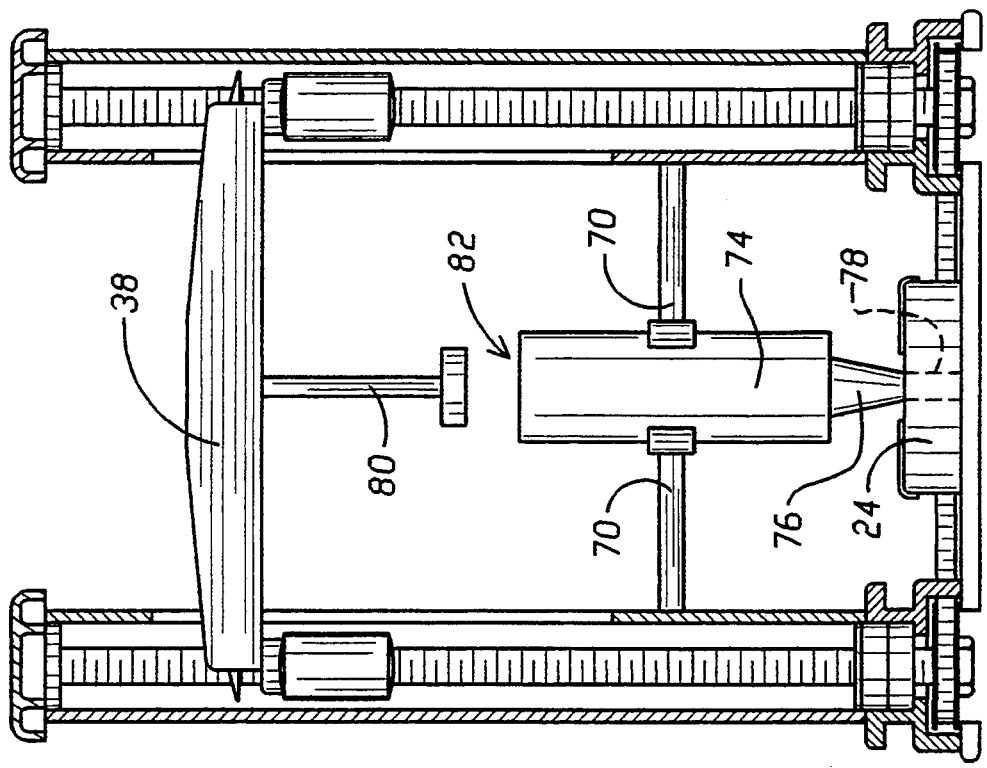
FIG. 6 is an elevation of the test fixture configured to perform a material tube extrusion test.

Another example of one way in which the test fixture 12 can be reconfigured is for performance of an extrusion rate test for standard material tubes, such as those often used in industry in conjunction with a gun for storage and distribution of elastomers or other materials. Referring then to FIG. 6 there is shown a test fixture 12 with the upper and lower fixture adaptors 32, 40, respectively, removed. Arms 70 having holders 72 are affixed to the tubular housings 34 to support a material tube 74 within the test fixture while permitting vertical movement of the material tube. The spout 76 of the material tube 74, cut to provide a predetermined opening therein, is inserted into a passageway 78 in the load cell 24. A plunger 80 is affixed to the central carriage 38 and extends downwardly to fit within the end 82 of the material tube 74 opposite the spout 76. The portable computer 20 initiates a test by sending appropriate instructions to the drive controller 14 which causes the motor 22 to move the carriage 38 and affixed plunger 80 downwardly at a predetermined rate or pressure causing the material within the tube to be extruded through the opening in the spout 76 and the passage 78 in the load cell 24. Since the arms 70 and holders 72 permit vertical movement of the tube 74, the pressure exerted on the material therein by the plunger 80 is transferred to the load cell 24 through the spout 76 thus permitting detection of the corresponding force by the load cell. The force detected by the load cell 24 is then recorded and stored by the portable computer 20. Through the use of the test fixture 12 configured in this manner, the necessary force required to extrude a predetermined quantity of material from the tube can be determined as well as information relative to the flow characteristics of the material or characteristics of the material tube.

The ability to easily reconfigure the system to perform separate material tests allows easy characterization of a material and correlation of results since the portable computer 20 will have in its memory the results of the different tests. Thus, the flowability, curing rate, tack, etc. for a given material are readily available to aid the user in predicting the suitability of a specific material to a certain application as in certain environment conditions, for example.

Turning now FIGS. 7 through 12, there are shown a number of data flow/computer program flow chart diagrams describing in detail the operation of the portable universal test system 10 of the present invention. The test system includes a number of routines which can be initiated by depressing a function key to accomplish tasks such as configuring a test, running a test, etc. The function keys may be devoted to operations performed for a single test, such as a tack free time test, or to providing operations for several different types of tests such as adhesion and cohesion, extrusion rate, tack free time, etc. In the latter instance, the test fixture 12 is set up to perform a desired test and then the appropriate function key is selected to instruct the portable computer 20 and drive controller 14 to control the test fixture in accordance with the selected test.

Figure 7:
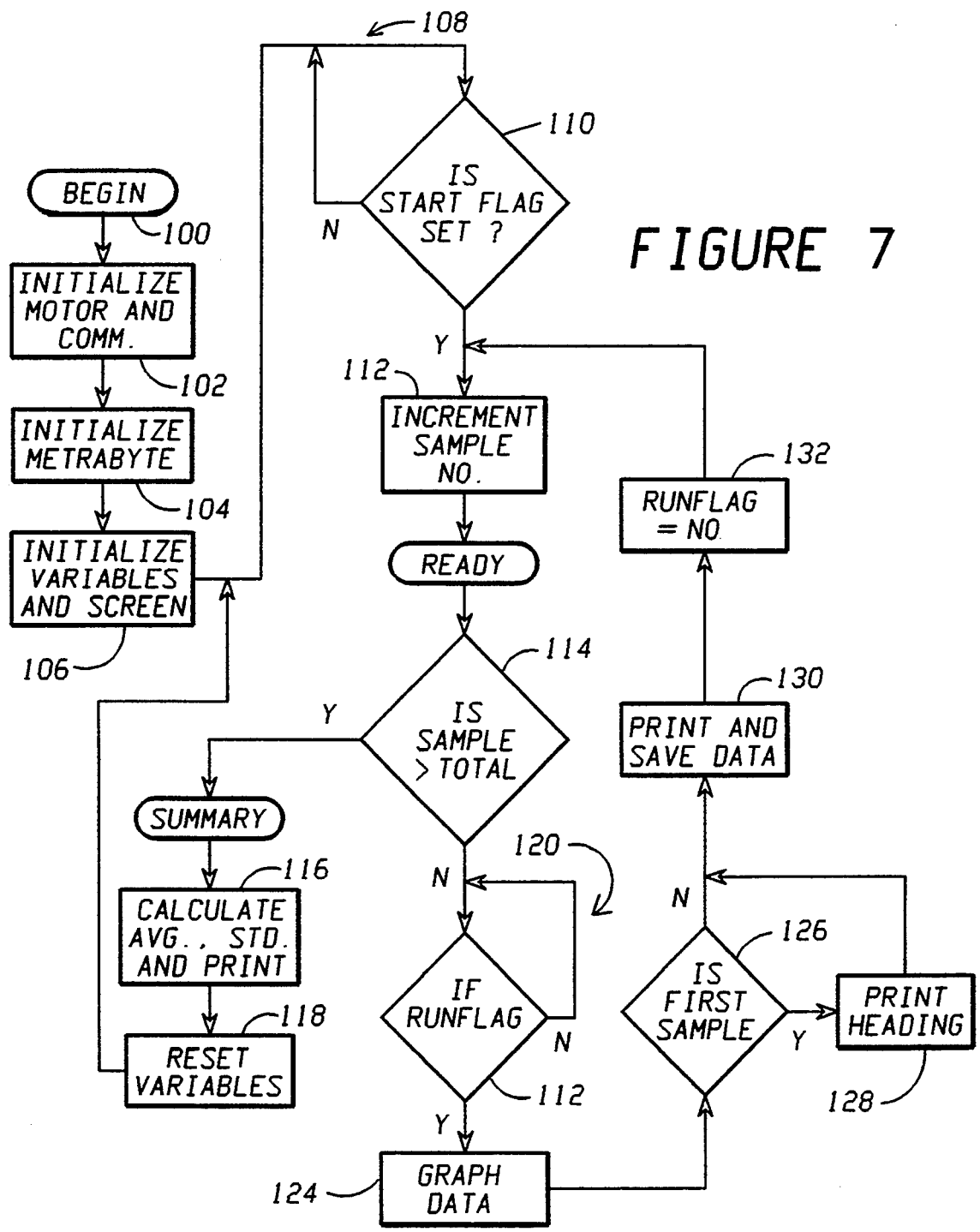
FIGS. 7 through 12 are flow diagrams illustrating an exemplary manner of performing a number of functions associated with the system of the present invention.

When the portable computer 20 is powered up, the portable computer will begin the routine illustrated in FIG. 7. The routine, labeled BEGIN, generally commands all the components in the system to perform their respective initialization functions and controls the system operation when the system is not performing a requested function. (Steps in the various flow charts are identified in the following text by a reference numeral contained within parentheses.) Upon entering the BEGIN routine (100), the routine initializes the motor 22 and motor controller 14 (102), initializes the interface 19 (104), and then initializes its internal variables and control flags and initializes the screen display (106). Once all initialization functions have been performed, the routine enters a standby loop (108) where it continually tests a control flag, called Startflag, to determine if a series of tests, such as tack tests, are in the process of being performed (110). If a series of tests are being performed, Startflag will have been set to "yes" in the interrupt driven START routine (400) discussed below and the BEGIN routine (100) will proceed to increment the sample number of the test (112) to keep track of which test of the series is next to be performed. The sample number is then checked to determine if the sample number is greater than the total number of tests to be performed indicating the completion of a test series (114). If a test series has been completed, then the averages of the test data as well as the standard deviation are calculated and the results are stored and printed (116). The control flags, including the Startflag and Runflag, are then reset (118) and the routine will continue in the standby loop (108) until it determines that another series of tests is being performed.

If the routine determines that tests have not been completed for all of the samples in a series (114), the routine will enter another standby loop (120) waiting for another test to be completed. The routine determines whether a test has been completed by checking the Runflag control flag, which is set to "yes" in the interrupt driven START routine described below once a test for a sample has been run (122). If Runflag has not been set to "yes", the routine will continue in the loop 120 until it determines that Runflag has been set to "yes" indicating the completion of a requested test (122). Once it is determined that a test has been completed, the accumulated data will be presented in graphical format (124), such as shown in FIG. 4 for a series of tests, and the routine will determine whether or not the results are for the first sample in a series of tests (126). If the results correspond to the first sample in a series of tests, headings indicating the sample type and testing parameters are primed for the test series (128) and the test data is printed with the corresponding headings and saved (130). If the accumulated data is determined to be other than for the first sample in a test (126) then the data is immediately printed and saved (130) without reprinting the heading. Since a test has been completed and the data recorded, the Runflag control flag is reset (132), the sample number is incremented (112) and the routine again determines whether tests have been performed for all samples (114) and either waits for another test to be performed (120) if the previously performed test was not the last in a series, or calculates averages, etc., for a test series (116), resets its control variables (118) and waits for new test series to be initiated (108) if a series has been completed.

Figure 8:
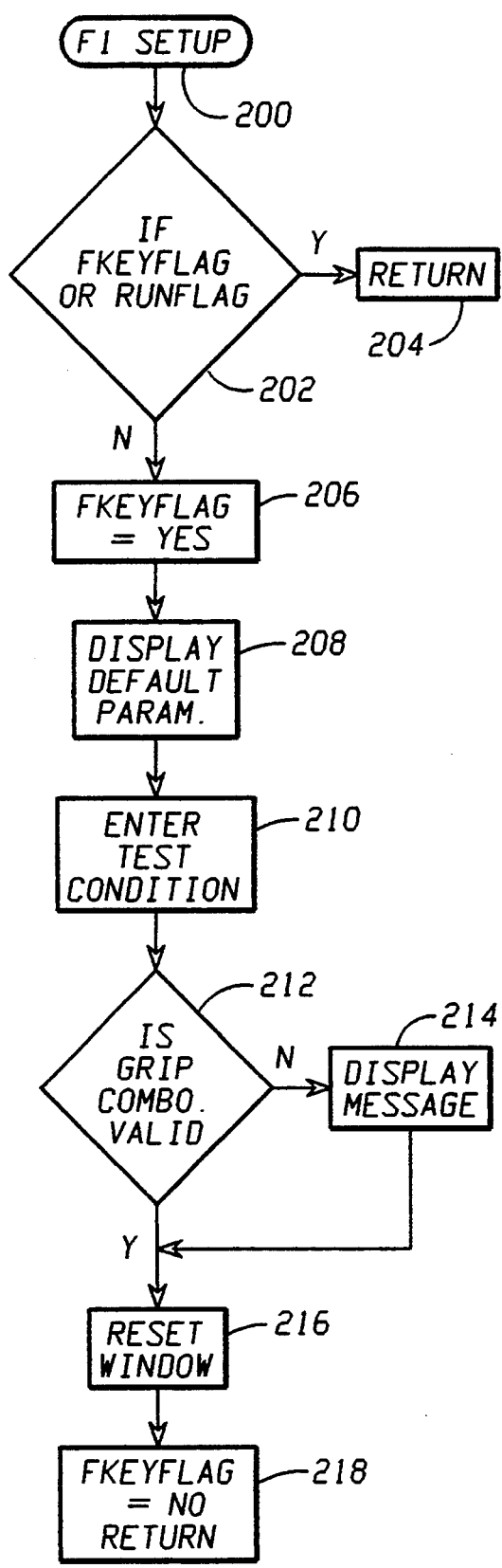

As is discussed above, the operator has control of a number of function selections through use of function keys on the keyboard. When a function key is depressed, the processor is interrupted allowing program control to jump from the BEGIN routine to one of the other function routines. Typically, after start up, the first routine which would be selected is the SETUP routine (200), a data flow diagram of which is shown in FIG. 8. The SETUP routine allows the user to configure the test, such as a tack free test, with the desired parameters.

Upon entering the SETUP routine the function key control flag, Fkeyflag, and the run flag control flag, Runflag, are checked to determine if another uncompleted interrupt function is being performed or if a test is being run (202). If Fkeyflag is set to "yes", indicating that another selected function is in the process of being executed, or if a test is currently being performed as indicated by Runflag being set to "yes", then program control will immediately return to the previously selected function (204). If not, then the function key control flag, Fkeyflag is set equal to "yes" indicating that a function is being performed, namely the SETUP function (206). (The Fkeyflag control flag is generally set to "yes" near the beginning of each of the interrupt functions selectable by use of a function key and is set to "no" generally at or near the end of each of those functions.) Once Fkeyflag has been set to "yes", the default parameters are displayed on the screen (208) and the user is prompted to enter the test conditions as well as to change any default parameters desired (210). Examples of such test conditions for a tack free time test are the test speed, the contact pressure, the dwell time and the grip combination. The grip combination represents the combination of the test fixture block 42 and cup 32. Once the appropriate parameters and test conditions have been entered, the SETUP routine checks to determine whether the grip combination is valid, or in other words whether the selected block and cup combinations are compatible (212). If not, a warning message is displayed indicating that the selected grip combination is not a valid choice (214). If the selected grip combination is valid, the screen window is reset (216) effectively removing the default parameters and test conditions from the screen and redisplaying a graph upon which data will be displayed once the test is performed (216). The Fkeyflag control flag is then set to "no" and program control is returned (218) to the BEGIN routine (100) where the program will idle in the standby loop 108 if a series of tests is not yet being performed or in the loop 120 if the routine is between tests. In the event that the SETUP routine (200) was called from the START routine (400), which is discussed below, then program control will return to that routine.

Figure 9:
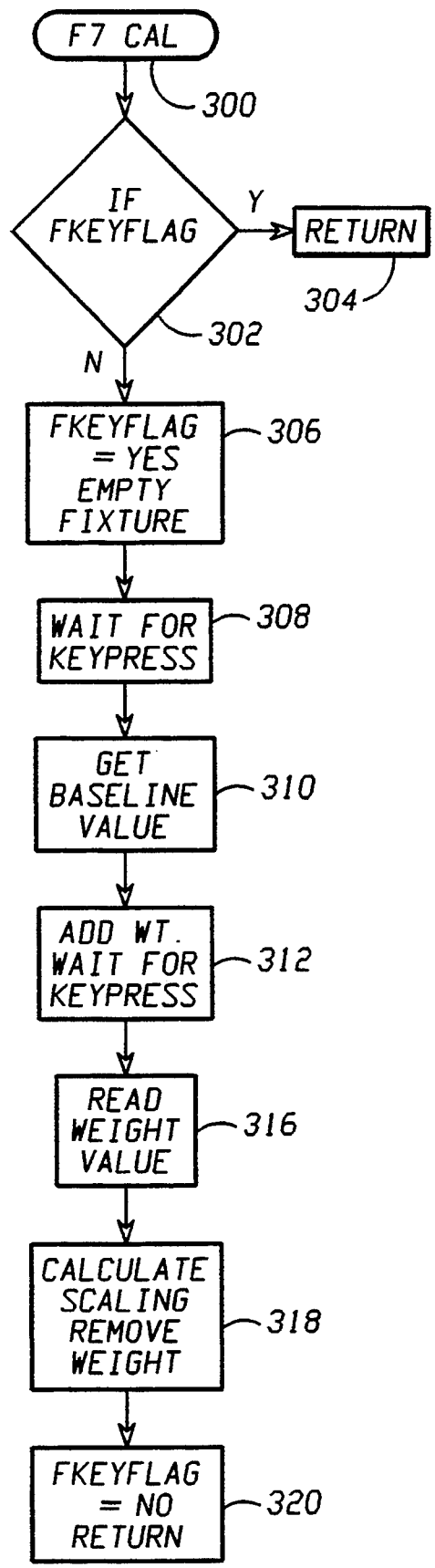

Another function oftentimes selected soon after power up or between a series of tests is calibration, which is performed by the calibration routine (300). The calibration routine is initiated by use of the F7 key and is shown in FIG. 9. Immediately upon entering the calibration routine (300) the Fkeyflag control flag is checked to determine whether another function key selected routine is being performed (302). If the Fkeyflag is set to "yes" indicating that another function is being performed, then program control immediately returns to the routine performing that function (304). If not, then the Fkeyflag is set to "yes" and the operator is instructed to make sure that the cup 33 of the test fixture 12 is empty (306) and the routine waits until the operator has responded that the test cup 33 is empty such as by depressing a key on the keyboard (308). The routine then obtains a baseline value, which is the voltage that the load cell 24 outputs to the signal conditioner 16 which is then digitized by the interface 19 and made available to the portable computer 20 (310). The routine then instructs the operator to place a known weight in the cup 33, thereby exerting a known force upon the load cell 24, and waits for the operator to depress a key indicating that the weight has been placed in the cup (312). Again the routine will obtain the weight value reading developed by the load cell transducer voltage as conditioned and amplified by the signal conditioner 16 and digitized by the interface 19 (316). By subtracting the baseline value from the value obtained with the known weight, a calibration scaling factor is calculated and the operator is instructed to remove the weight from the cup 33 (318). The Fkeyflag control flag is then set to "no" and program control returns (320) to the BEGIN routine (100) at loop 108 if a series of tests is not in the process of being run or loop 120 if the calibration routine was performed in between tests of a series.

Figure 10A:
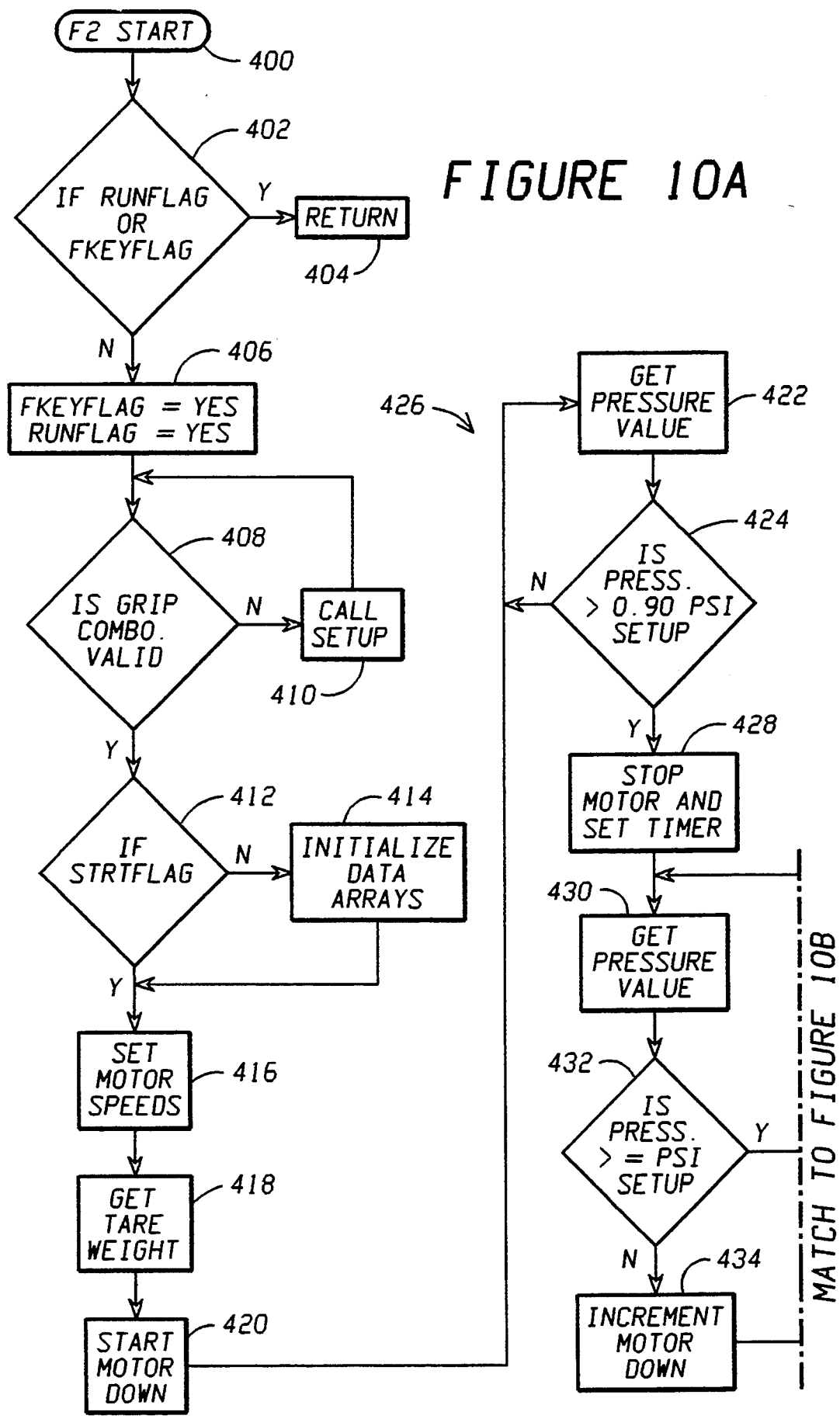
Figure 10B:
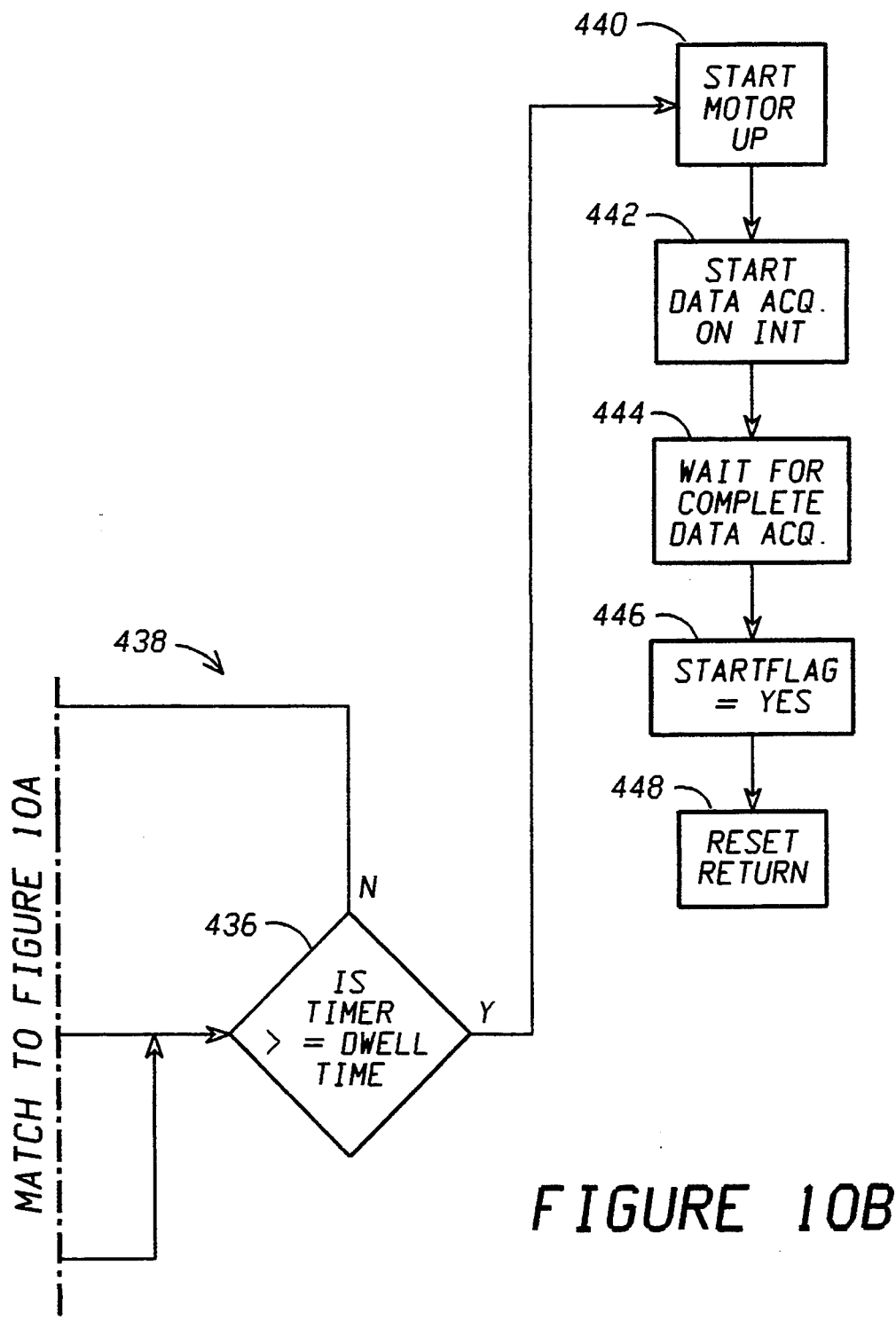

FIGS. 10A and 10B illustrate a data flow diagram for a routine which operates the test fixture in a manner to perform a tack free time test. This routine depends upon a specific configuration of the test fixture having a block 42 and cup 33 as is described above. To command the system 10 to perform the test, the operator hits the F2 key which sends an interrupt to the portable computer 20 whereupon it begins execution of the START routine 400. The START routine first checks the Runflag and Fkeyflag control flags to determine whether another test is concurrently being run or if the START routine was called while another function key select routine was being performed (402). If so, then program control is immediately returned to continue execution of instructions being performed in the routine when the F2 key was hit (404). If neither Runflag nor Fkeyflag is set to "yes", then both are set to "yes" to indicate that the START routine is being performed and that a run, or sample test, is in progress (406). The grip combination, i.e., the combination of the selected block 42 and test cup 33, is then checked to determine whether the selected block and cup can be employed together (408). If not, then the SETUP routine is called from within the START routine (410) wherein the operator is instructed to enter a new grip combination. This combination is again checked (408) and if the grip combination is valid, the contacting surface area between the block 42 and test cup 33 is calculated for later use in convening force data detected by the load cell 24 into pressure data. The Startflag control flag is then checked to determine whether the current test is other than the first of a series of tests (412). If Startflag is set to "no", then the current test is the first test of a series and the data arrays which hold the data for a series of sample tests are reinitialized (414). The speed for the motor 22 is then set and transmitted to the motor controller 14 over the RS-232 bus 25. The tare weight, or the force that the test cup 33 filled with a sample exerts on the load cell 24, as conditioned and amplified by the signal conditioner and sampled by the interface 19 is then obtained (418). The routine instructs the drive controller 14 to send the appropriate drive signals to the motor 22 to begin lowering the block 42 toward the cup 33 at the rate selected by the user during execution of the SETUP routine (420). The routine then continuously obtains force data corresponding to the output of the load cell 24 (422) and converts it to pressure data based on the contacting surface area between the block 42 and cup 33. The resultant pressure data is compared to a value which is 90% of the pressure set point, Setpt (424). The routine continues in loop 426 obtaining pressure values (422) and testing them (424) to determine whether the sensed pressure exceeds 90% of the pressure set point.

Once the sensed pressure exceeds 90% of the pressure set point, the motor 22 is stopped and a timer is set to begin timing of the tack-free time test (460). The motor 22 is then placed in an incremental mode allowing fine adjustment of the motor position. Another pressure value is then obtained from the load cell 24 corresponding to the pressure the block 42 is exerting on the sample in the cup 33 (430) and that value is compared to see whether it is greater than or equal to the set point pressure (432). If the sensed pressure has not yet reached the pressure set point value, the motor is incremented downwardly thus increasing the force the block 42 exerts on the sample (434). If the sensed pressure is equal to or greater than the set point pressure, the force the block 42 exerts on the sample is not adjusted. The timer is then checked to determine whether it is greater than or equal to the dwell time (436), and, if not, a pressure value is again obtained (430), the sensed pressure is compared to the pressure set point (432) and the motor is incremented to increase the force exerted on the sample (434), if necessary. The routine remains in this loop (438) obtaining pressure values and comparing them to the set point, making motor adjustments and comparing the timer value to the dwell time until the dwell time has been exceeded. Note that since some sample materials for which the test may be performed may tend to flow in response to the pressure exerted from the foot 42, the pressure is continually checked within the loop (438) and the motor incremented to maintain the desired pressure on the sample material.

Once it has been determined that the block 42 has maintained contact with the sample in the cup 33 for a time which is equal to or exceeds the dwell time (436), the routine commands the motor drive controller 14 over the RS-232 bus 25 to send the appropriate signals to the motor 22 to reverse direction and raise the block 42 at the default speed or other speed specified by the operator during execution of the SETUP routine (440). At this point an interrupt is sent to the data interface 21 instructing it to begin sampling data from the signal conditioner 16 at the present rate, for example, 50 Hz, over the time during which it takes the motor 22 to raise the block 42 the predetermined distance, such as one-half inch, above the cup 33 (442). The routine then waits to be instructed from the computer 20 that the motor 22 has raised the block 42 the required amount and that data acquisition is complete (444). The Startflag control flag is then set to "yes" (446), indicating that at least one test sample out of a series of tests has been performed, whereupon the routine variables are reset and program control returns to the BEGIN routine (100).

Program control returns from the START routine (400) to the BEGIN routine (100), FIG. 7, in the standby loops 110 or 120. Since the Startflag and Runflag control flags were both set in the START routine to "yes", the respective loops are exited, the sample number is incremented if the test were the first in a series (112) and the acquired data is correlated and graphed (124) and printed and saved as necessary (126, 128, 130). The Runflag control flag is then reset to "no" (132) and the sample number is incremented (112). (This is the second time that the sample number is incremented between tests if the concluded test were the first in a series.) The routine then idles in the standby loop 120 waiting for another test in the series to be performed unless tests have been performed for the total number of samples, whereupon the program summary is printed (116) and the variables are reset to indicate that the test series is over (118). The routine then waits within the standby loop 108 waiting for the operator to select another function key.

Figure 11:
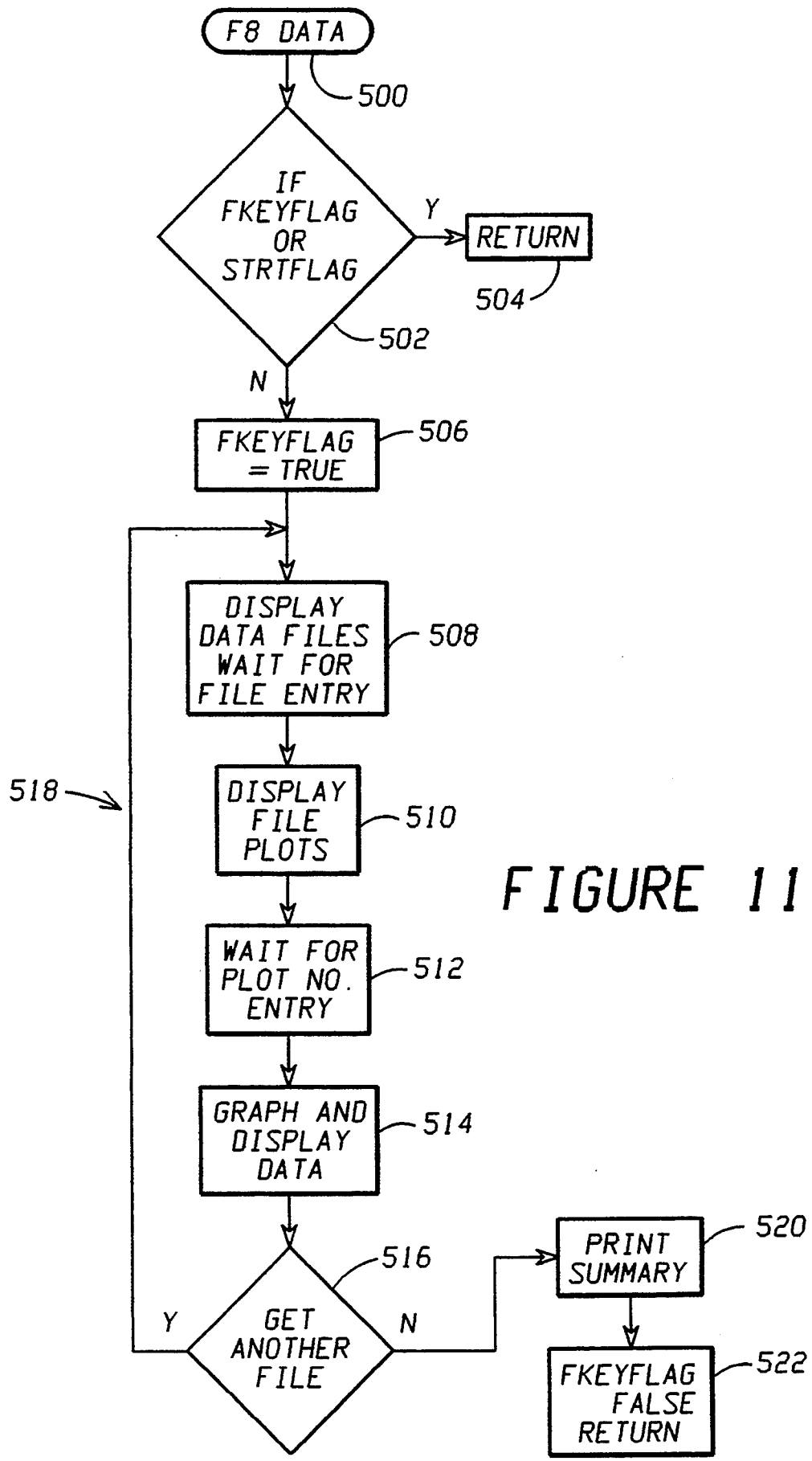

The user is also provided with the option of viewing any of the stored data files or concurrently plotting data for more than one file to facilitate comparisons. Such an option is provided through the DATA routine (500), as shown in FIG. 11. The DATA routine is an interrupt driven route initiated through the use of the F8 function key. The routine initially checks the Fkeyflag and Startflag control flags to see if either is set to "yes" (502). If the Fkeyflag is set to "yes", indicating that another function is concurrently being executed, or Startflag is set to "yes", indicating that only a portion of a series of tests has been completed, program control returns back to the routine from which the DATA routine was called (504). If neither Fkeyflag nor Startflag is set to "yes" then execution of the DATA routine is permitted to continue and Fkeyflag is set to "yes" (506). The available data files are then displayed and the routine waits for the operator to select the appropriate file for display (508). Upon selection of a file, the routine displays the plots for each file (510) and waits for the user to choose which plot of the selected file is desired to be displayed (512). The selected data is then graphed and the data is displayed (514) and the user is prompted whether another file is to be displayed (516). If so, then the routine will again display the files and prompt the user to select which files are desired for display and will display the appropriate data (508, 510, 512, 514). The routine will continue within this loop 518 until the user responds that all desired data has been graphically displayed. A summary of the data files selected is then printed (520), the Fkeyflag control flag is set to "no" and program control returns to the BEGIN routine (100) from which the function was called (520).

Figure 12:
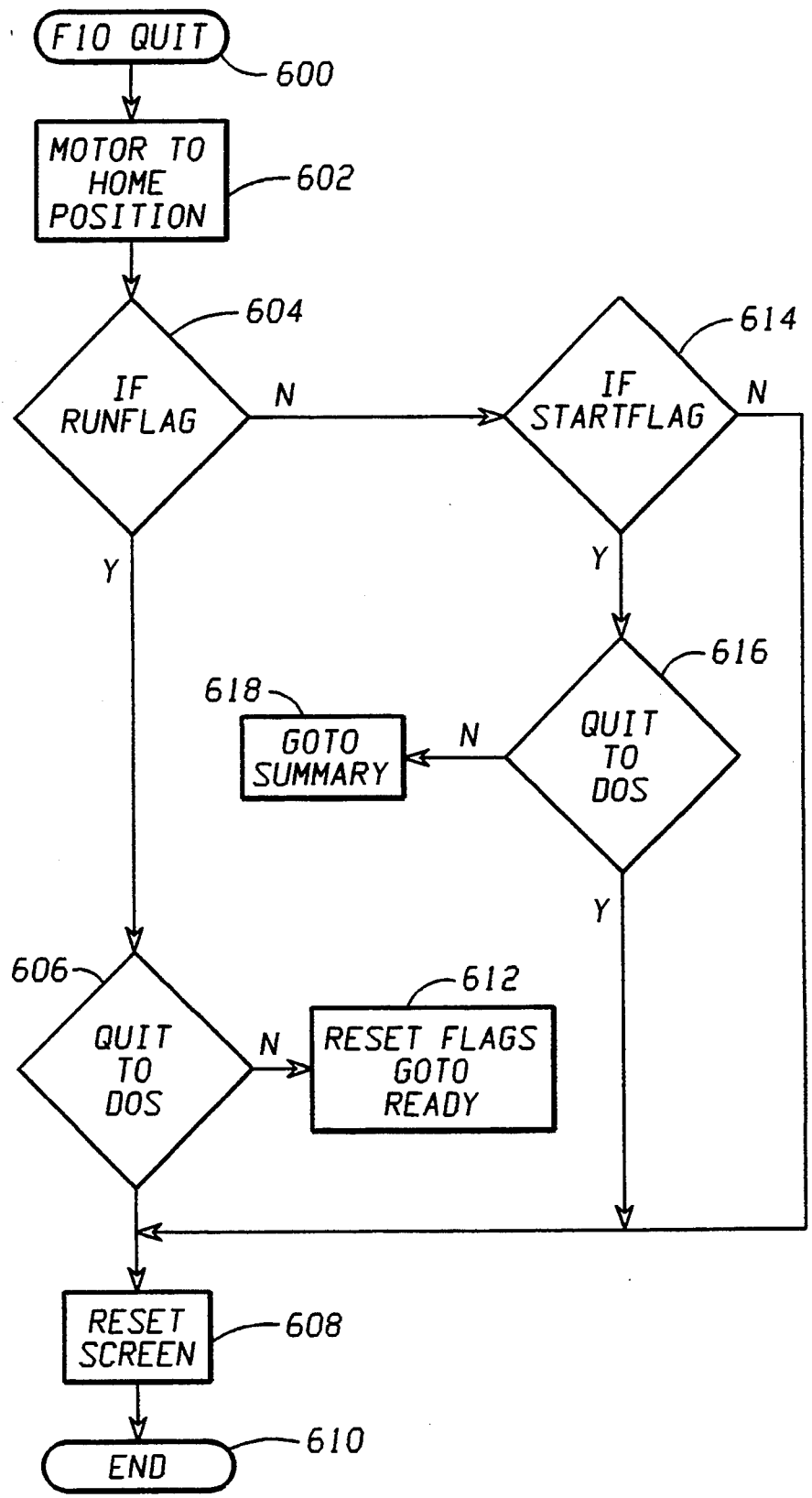

The system 10 also provides the user with the option to quit at any time, including while a test is being performed, by depressing the F10 key. The QUIT routine (600) is shown in FIG. 12. Once the user selects the F10 key the routine currently being executed is interrupted and the QUIT routine is executed. The QUIT routine immediately instructs the drive controller 14 to send the appropriate drive signals to the motor 22 to return the block 42 and carriage 38 to their home position (602). The routine then determines whether a test was currently being performed when the F10 key was depressed by checking the Runflag control flag (604). If Runflag is set to "yes" a test was in progress and the user is prompted whether immediately to exit to the computer operating system, such as DOS (606). If the user chooses to quit to DOS then the screen is reset (608) and program control immediately returns to the DOS operating system (610). If the user has selected not to exit to DOS, then the appropriate flags are reset and program control returns to the BEGIN routine at a location in the data flow diagram of FIG. 7 marked READY, whereupon a new test can be performed (612). If Runflag is set to "no" (604), indicating that a test is not currently in progress, the routine will check the Startflag control flag (614). If Startflag is set to "yes", indicating that at least one test of a series of tests has not been completed, then the user is prompted whether to exit to DOS or to have a summary of test data performed (616). If the user chooses to quit to DOS, the screen is reset (608) and program control returns to the operating system (610). If the user has selected not to quit to DOS, then program control returns (618) to the BEGIN routine (100) at the location marked SUMMARY, as shown in the data flow diagram of FIG. 7, whereupon a summary for the completed tests is performed and the results are calculated and printed (116, 118). In the event that Startflag was set to "no" (614), indicating that the system was not currently performing any of a series of tests, the screen is reset (608) and program control immediately returns to DOS If a user wished to follow a tack test with an extrusion rate test, for example, the user would simply replace the cup 33 and block 42 with the chamber and plunger described above. The user would then depress an appropriate function key to cause the execution of a set up routine similar to that described relative to FIG. 8, wherein appropriate testing parameters would be entered, such as the constant force to be applied to the sample and the test duration. The user would then depress another function key to initiate the extrusion rate test and control of one or a series of extrusion rate tests would be accomplished through the BEGIN routine described above. Other tests, such as the material tube extrusion rate test and adhesion tests described above, could be initiated and executed in a similar fashion. In some instances, it is desirable to follow a series of tests for a specific material characteristic or property with a series of tests for a different material characteristic or property. For example, a user may choose to perform a series of tack free time tests for an elastomer cured for 5, 10, 15, 20, etc. minutes and then follow that with an extrusion rate test for that elastomer cured over the same durations. In other instances, it may be desirable to intersperse tests for one material property with a test for another material property. In such a case a test for tack free time may be followed by an extrusion rate test both at the same curing durations, with appropriate changes of the test fixture in between tests.

Given the description above and the accompanying figures, it is believed that a person of ordinary skill in the an could convert the description into a suitable programing language with a reasonable amount of ordinary effort and within a reasonable period of time. Further, while the particular example described above related to a specific materials test, namely, a tack free time test, it would be appreciated that the portable universal material test system could include code in addition to or instead of that for the tack free time test to permit the test system to perform other tests, such as an adhesion and cohesion test, an extrusion rate test, an indentation hardness test, or an adhesion-in-peel test, for example.

What is claimed:

1. A system for determining material properties of a sample comprising:

a testing device, including a base, a load sensing element, a motor and a test apparatus, said test apparatus being adaptable to perform a plurality of different material tests, said motor being coupled to said test apparatus to drive at least a portion of said test apparatus in accordance with a selected test and said load sensing element coupled to said test apparatus to sense a force transmitted by said test apparatus;

control means coupled to said motor for controlling the operation of said motor in response to a signal from said load sensing element; and processing means coupled to said control means and said load sensing element for processing the results of a test as sensed by said load sensing element.

2. The system of claim 1, wherein said test apparatus includes a cup for holding said sample and a block for contacting the sample in said cup.

3. The system of claim 2, wherein said block is constructed of brass.

4. The system of claim 2, wherein said block is constructed of a construction material in which said material would typically contact in actual use.

5. The system of claim 2, wherein said block is adapted to receive a sample.

6. The system of claim 2, wherein said cup is in fixed relative position to said load sensing element while said block is moveable with respect to said load cell.

7. The system of claim 1, wherein said test apparatus is adapted to receive interchangeable testing elements each adapted to perform a different test.

8. The system of claim 7, wherein said control means controls said testing device in accordance with the interchangeable testing elements received in said test apparatus.

9. The system of claim 1, wherein said load sensing element is in a fixed position relative to said base.

10. The system of claim 1, wherein said processing means includes means for storing and correlating results of plural material tests.

11. The system of claim 1, wherein said system is portable.

* * * * *